US005985933A

United States Patent [19]
Zeitlin

[11] Patent Number: 5,985,933
[45] Date of Patent: *Nov. 16, 1999

[54] METHODS FOR TREATING CENTRAL AND PERIPHERAL NERVE PAIN

[75] Inventor: Andrew L. Zeitlin, Millington, N.J.

[73] Assignee: Celgene Corporation, Warren, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/786,749

[22] Filed: Jan. 24, 1997

[51] Int. Cl.$^6$ ........................ A61K 31/135; A61K 31/40; A61K 31/445; A61K 31/55

[52] U.S. Cl. ........................ 514/651; 514/428; 514/317; 514/212

[58] Field of Search ........................ 514/651, 428, 514/317, 212; 548/570; 546/236; 540/609; 568/584

[56] References Cited

U.S. PATENT DOCUMENTS 3,954,872  5/1976  Koppe et al. ........................ 260/570.7

FOREIGN PATENT DOCUMENTS

| 2337021 | 2/1975 | Germany. |
|---|---|---|
| 6903772 | 3/1970 | South Africa. |
| 2246774 | 2/1992 | United Kingdom. |
| WO 97/271969 | 7/1997 | WIPO. |

OTHER PUBLICATIONS

Ackerman, III, et al., "The Management fo Oral Mexiletine and Intravenous Lidocaine to Treat Chronic Painful Symmetrical Distal Diabetic Neuropathy", *KMA J.*, 1991, 89, 500–501.

Awerbuch et al., "Mexiletine for thalamic pain syndrome", *Internal J. Neuroscience*, 1990, 55, 129–133.

Backonja, "Local Anesthetics as Adjuvant Analgesics", *J. Pain Sympt. Man.*, 1994, 9(8), 491–499.

Calcutt et al., "Impaired induction of vasoactive intestinal polypeptide after sciatic nerve injury in the streptozotocin–diabetic rat", *J. Neurol. Sci.*, 1993, 119, 154–160.

Campbell, "Mexiletine", *New Eng. J. Med.*, 1987, 316(1), 29–34.

Chabal et al., "The use of oral mexiletine for the treatment of pain after peripheral nerve injury", *Anesthesiology*, 1992, 76, 513–517.

Chaplan, S.R. et al., "Quantitative assessment of allodynia in the rat paw", *J. Neurosci. Methods*, 1994, 53, 55–63.

Chaplan et al., "Prolonged alleviation of tactile allodynia by intravenous lidocaine in neuropathic rats", *Anesthesiology*, 1995, 83, 775–785.

Courteix et al., "Study of the sensitivity of the diabetes–induced pain model in rats to a range of analgesics", *Pain*, 1994, 57, 153–160.

Colclough et al., "Mexiletine for chronic pain", *Lancet*, 1993, 342, 1484–1485.

Dejgard et al., "Mexiletine for treatment of chronic painful diabetic neuropathy", *Lancet*, 1988, 2, 9–11.

Franchini et al., "Stereoselectivity in Central Analgesic Action of Tocainide and Its Analogs", *Chirality*, 1993, 5, 135–142.

Grech–Belanger et al., "Stereoselective disposition of mexiletine in man", *Br. J. Clin. Pharmacol.*, 1986, 21, 481–487.

Greenwald et al., "The prevalence of pain in four cancers", *Cancer*, 1987, 60, 2563–2569.

Harbilas, "Mexiletine for Pain?", *Hos. Pharm.*, 1995, 30, 720 and 723.

Hardman, J.G. (ed.), Goodman & Gilman's *The Pharmacological Basis of Therapeutics*, 9th ed., McGraw–Hill, 1996, p. 219.

Hill et al., "Determinants of stereospecific binding of Type I antiarrhythmic drugs to cardiac sodium channels", *Molec. Pharmacol.*, 1988, 34, 659–663.

Kalichman et al., "Local anesthetic–induced conduction block and nerve fiber injury in streptozotocin–diabetic rats", *Anesthesiology*, 1992, 77, 941–947.

Kamei et al., "Antinociceptive effect of mexilitene in diabetic mice", *Res. Commun. Chem. Pathol. Pharmacol.*, 1992, 77, 245–248.

Kastrup, "Clinical Note: Intravenous lidocaine infusion—a new treatment of chronic painful diabetic neuropathy?", *Pain*, 1987, 28, 69–75.

Kim et al., "An experimental model for peripheral neuropathy produced by segmental spinal nerve ligation in the rat", *Pain*, 1992, 50, 355–363.

Kreeger et al., "New Antiarrhythmic Drugs: Tocainide, Meiletine, Flecainide, Encainide, and Amiodarone", *Mayo Clin. Proc.*, 1987, 62, 1033–1050.

Kubota et al., "Relief of severe diabetic truncal pain with mexiletine", *J. Med.*, 1991, 22(4 & 5), 307–310.

(List continued on next page.)

*Primary Examiner*—Phyllis G. Spivack
*Attorney, Agent, or Firm*—Woodcock Washburn Kurtz Mackiewicz & Norris LLP

[57] ABSTRACT

Methods of treating painful neuropathies are provided comprising administering compounds comprising the (S)-isomer of chiral compounds having the formula:

wherein R1 is C1–C5 hydrocarbyl, R2 and R3 are independently C1–C5 hydrocarbyl or H, R4 is C1–C5 hydrocarbyl, R3 and R4 may optionally be joined together to form a 5, 6 or 7 membered ring system, or a pharmaceutically acceptable salt thereof, substantially free of the (R)-isomer.

5 Claims, No Drawings

OTHER PUBLICATIONS

Kwok et al., "Pharmacokinetics of mexiletine enantiomers in healthy subjects. A study of the in vivo serum protein binding, salivary excretion and red blood cell distribution of the enantiomers", *Xenobiotica*, 1995 25(10):1127–1142.

Lindstrom et al., "The analgesic effect of tocainide in trigeminal neuralgia", *Pain*, 1987, 28, 45–50.

Marchettini et al., "Lidocaine test in neuralgia", *Pain*, 1992, 48, 377–382.

Monk et al., "Mexiletine: a review of its pharmacodynamic and pharmacokinetic properties and therapeutic use in the treatment of arrhythmias", *Drugs*, 1990, 40(3), 374–411.

Nishiyama et al., "Mexiletine for painful alcoholic neuropathy", *Internal Medicine*, 1995, 34(6), 577–579.

Paggioli et al., "Intravenous and Oral Anesthetics in Pain Management: Reflections on Intravenous Lidocaine and Mexiletine", *Pain Digest*, 1995, 5, 69–72.

Pfeifer et al., "A highly successful and novel method for treatment of chronic painful diabetic peripheral neuropathy", *Diabetes Care*, 1993, 16(8), 1103–1115.

Petersen et al., "Chronic pain treatment with intravenous lidocaine", *Neurological Research*, 1986, 8, 189–190.

Portenoy, "Pharmacologic approaches to the control of cancer pain", *J. Psychosoc. Oncol.*, 1990, 8, 2–3 and 75–107.

Stracke et al., "Mexitetine in the Treatment of Diabetic Neuropathy", *Diabetes Care*, 1992, 15(11), 1550–1555.

Tanelian et al., "Neuropathic pain can be relieved by drugs that are use–dependent sodium channel blockers: lidocaine, carbmazepine, and mexiletine", *Anesthesiology*, 1991, 74, 949–951.

Turgeon et al., "Resolution and electrophysiological effects of mexiletine enantiomers", *J. Pharm. Pharmacol.*, 1991, 43, 630–635.

Wilkie, "Cancer pain management: State–of–the–art nursing care", *Nurs. Clin. North Am.*, 1990, 25(2), 331–343.

Xu et al., "Systemic mexiletine relieves chronic allodynia–like symptoms in rats with ischemic spinal cord injury", *Anesth. Analg.*, 1992, 74, 649–652.

Yaksh et al., "The spinal pharmacology of facilitation of afferent processing evoked by high–threshold afferent input of the postinjury pain state", *Curr. Opin. Neurol. Neurosurgery*, 1993, 6, 250–256.

Vozeh et al., "Population pharmacokinetic parameters in patients treated with oral mexiletene", *Eur. J. Clin. Pharmacol.*, 1982, 23, 445–451.

METHODS FOR TREATING CENTRAL AND PERIPHERAL NERVE PAIN

FIELD OF THE INVENTION

The present invention relates to methods of treating painful neuropathies such as diabetic polyneuropathy, peripheral neuropathy and alcoholic polyneuropathy.

BACKGROUND OF THE INVENTION

Racemic mexiletine has been administered orally to relieve the symptoms of a number of painful neuropathies including painful diabetic neuropathy; Dejard, et al., *Mexiletine for treatment of chronic painful diabetic neuropathy, The Lancet*, 2:9, 9–11 (1988); pain due to acute or chronic nerve injury; Tanelian, et al., *Neuropathic pain can be relieved by drugs that are use-dependent sodium channel bockers, lidocaine, carmazepine and mexiletine, Anesthesiology*, 74: 949–951 (1991); alcoholic polyneuropathy; Sakuta, et al., *Mexiletine for painful alcholic neuropathy, Internal Medicine*, 34: 577–579 (1995); chronic pain associated with radiation therapy; Colclough, et al., *Mexiletine for chronic pain, The Lancet*, 342: 1484–1485 (1993); thalamic pain syndrome, Awerbuch, G. I., et al., *Mexiletine for thalamic pain syndrome, Intern. J., Neuroscience*, 55:129–133 (1990); and diabeic truncal pain; Kubota, K., et la., *Relief of severe diabetic truncal pain with mexiletine, J. Med.*, 22: 307–310 (1991).

The overall metabolic disposition of mexiletine enantiomers in healthy human subjects is non-stereoselective; McErlane et al., *Xenobiotica*, 25(10):1127–1145 (1995). However, another study of stereoselective glucuronidation of enantiomers of mexiletine suggests a stereoselective glucuronidation of the (R)-enantiomer. Grech Belanger, et al., *Stereoselective disposition of mexiletine in man, Br. J. Clin. Pharmacol.*, 21:481–487 (1986). The cardiac electrophysiological effect of mexiletine in rats and dogs is also stereospecific. Hill demonstrated the binding affinity of (R)-mexiletine is twice that of (S)mexiletine for cardiac sodium channels. Hill, R. J. et al., *Determinants of stereospecific binding of type I antiarrhythmic drugs to cardiac sodium channels, Molec. Pharmacol.*, 34:659–663 (1988).

Racemic mexiletine is also an antiarrhythmic agent and studies have shown that the (R)-enantiomer exhibits greater antiarrhythmic properties than the (S)-enantiomer in dogs. Turgeon, J. et al., *Resolution and Electrophysiological effects of mexiletine enantiomers, J. Pharm. Pharmacol.*, 43:630–635 (1991).

While racemic mexiletine has shown efficacy for a variety of painful neuropathies, its proarrhythmic properties are a cause for concern as are a number of serious non-cardiac adverse side effects all of which limit its use. Such effects include tremors, diplopia, nausea and vomiting, and occur in up to 70 percent of patients. These adverse side effects are closely related to the plasma concentration of racemic mexiletine, and such adverse effects are usually lessened with reductions in dosage. However, reduced dosage often results in reduced therapeutic efficacy. Campbell, R. W. F., *Mexiletine, N. Eng. J. Med.*, 316:29–34 (1987).

Thus, an improved method of treating neuropathic pain with a sodium channel blocker that has reduced or eliminated adverse side effects is greatly desired.

SUMMARY OF THE INVENTION

In accordance with some aspects of the present invention are provided methods of treating painful neuropathies comprising administering a therapeutically effective amount of a pharmaceutical compound comprising the(S)-isomer of a chiral compound having the formula:

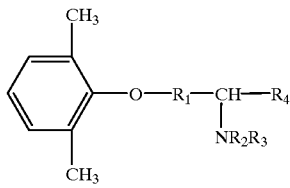

Formula I wherein R1 is C1–C5 hydrocarbyl, R2 and R3 are independently C1–C5 hydrocarbyl or H, R4 is C1–C5 hydrocarbyl, R3 and R4 may optionally be joined together to form a 5, 6 or 7 membered ring system, or a pharmaceutically acceptable salt thereof, and the compound is substantially free of the (R)-isomer.

In other embodiments of the present invention are provided pharmaceutical compounds for treating painful neuropathies comprising transdermal delivery patch including a therapeutically effective amount of a pharmaceutical compound comprising the (S)-isomer of a chiral compound having Formula I.

In still other embodiments of the present invention are provided pharmaceutical compounds for treating painful neuropathies comprising therapeutically effective amounts of pharmaceutical compounds comprising the (S)-isomer of a chiral compound having Formula I and one or more pharmaceutically acceptable exipients.

DETAILED DESCRIPTION OF THE INVENTION

Although racemic mexiletine has been used for relief of painful neuropathies, single-isomer mexiletine has never been used as a therapy for the relief of painful neuropathies. Furthermore, until now, the use of mexiletine for painful neuropathies has been limited by concern about its proarrhythmic properties as well as dose-concentration related toxicity.

It has previously been proposed that both the antiarrhythmia and anesthetic properties of mexiletine are related to the same mechanism of Na+ channel blockade. Despite findings that the (R)-isomer of mexiletine has greater than two times more antiarrhythmic properties than the (S)-isomer, it has now been discovered, in accordance with this invention, that that the pain relieving properties of racemic mixtures of mexiletine and other related compounds of the present invention are due to the (S)-isomer. Surprisingly, little or no pain relieving properties appear to be associated with the (R)-isomer of such compounds. While not wishing to be bound to any particular theory, it is believed that this phenomena may be due to structural and/or mechanistic differences in the way sodium channel blockers bind to neuronal and cardiac sodium channels.

Thus, in accordance with the present invention, methods of treating painful neuropathies are provided comprising administering a therapeutically effective amount of a pharmaceutical compound comprising the (S)-isomer of a chiral compound having the formula:

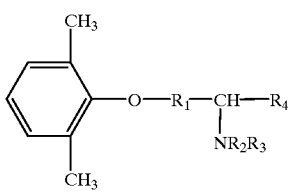

Formula I wherein R1 is C1–C5 hydrocarbyl, R2 and R3 are independently C1–C5 hydrocarbyl or H, R4 is C1–C5 hydrocarbyl, R3 and R4 may optionally be joined together to form a 5, 6 or 7 membered ring system, or a pharmaceutically acceptable salt thereof, and the compound is substantially free of the (R)-isomer.

Hydrocarbyl as used herein refers to an organic radical composed primarily of carbon and hydrogen. Hydrocarbyl groups of the present invention may be straight or branched chain alkyl, alkenyl or alkynyl groups which may, optionally, be substituted with hydroxy or halogen groups. Typical hydrocarbyl groups of the present invention include methyl, ethyl, n-propyl, isopropyl, n-butyl, sec-butyl, t-butyl, n-pentyl, n-hexyl and the like.

Although the compounds depicted by Formula I are generally preferred in accordance with methods of the present invention, substitutions and modifications of the general formula may be made as would be appreciated by one skilled in the art. For instance, the phenyl methyl groups may be substituted such as with ethyl, propyl, trimethyl, trifloromethyl and the like. Other ring substitutions, especially in the para position are also envisioned in some aspects of the invention.

In still other embodiments of the present invention, the ether linkage may be substituted with, for example, an amide linkage.

It may also be desirable to substitute the hydrogen of the carbon atom alpha to the amine group of Formula I with a hydrocarbyl group such as susbstituted or unsubstituted C1–C5 hydrocarbyl. Additionally, it may be desireable in some aspects of the present invention to provide additional substitutions and/or increased chain length of R2 and R3, while limiting polarity. These modifications are anticipated to cause improved pharmacologic properties, thereby enhancing their analgesic effectiveness.

The term "substantially free of the (R)-isomer" as used herein means that the composition contains at least 90% by weight of the (S)-isomer, and 10% or less by weight of the (R)-isomer. In the most preferred embodiment, the composition contains at least 99% by weight of the (S)-isomer and 1% or less of the (R)-isomer.

Racemic mixtures of compounds of Formula I are known. For instance, racemic mexiletine and analogs thereof are described. See U.S. Pat. No. 3,954,872. Isomers of compounds of Formula I can be prepared by, e.g., minor modification of the techniques described in Turgeon et al., *J. Phaz-m. Pharmacol.*, 43: 630–635 (1991), or UK Application GB 2246774A, filed Aug. 7, 1990 in the name of Shell International Research Maatschappij B. V.

Methods of the present invention may be used to treat painful neuropathies. Painful neuropathy and central and peripheral nerve pain, as used herein may refer to conditions including, but not limited to diabetic polyneuropathy, peripheral neuropathy, thalamic pain syndrome, trauma induced pain due to chronic nerve injury, alcoholic polynueropathy, neuropathic pain associated with radiation therapy, AIDS and cancer.

Therapeutic effectiveness of methods of the present invention is meant to refer to partial or entire relief from the pain associated with painful neuropathies, resulting in enhanced quality of life. Furthermore, in accordance with the present invention, such relief from pain is achieved with reduced or eliminated side-effects traditionally associated with treatment of such conditions with racemic mexiletine and related antiarrhythmic anticonvulsant and anesthetic compounds.

(S)-mexiletine and other (S)-isomers of Formula I are more effective for the treatment of painful neuropathies than the racemate at a lower dosage range (50–600 mg/day). Therpeutically effective amount of (S)-isomer may be dosed at about two (2) times lower dosage than the dosage generally prescribed for the racemic mixture. This reduced dosage is accompanied by concomitant reduced dose-related side-effects. For example, racemic mexiletine has a narrow therapeutic-toxic concentration range of 0.5–2.0 $\mu$g/ml. Monk, J. P. et al., *Mexiletine: a review of its pharmacodynamic and pharmacokinetic properties and therapeutic use in the treatment of arrhythmias*, Drugs, 40:374–411 (1990). The (S)-isomer has a lower side effect profile and thus a broader therapeutic-toxic range of 0.25–4 $\mu$g/ml.

Pharmaceutically acceptable salts of compounds of Formula I are also useful in methods of the present invention. Pharmaceutically acceptable salts useful in the invention include, but are not limited to salts of hydrochloric acid, hydrobromic acid, fumaric acid, oxalic acid, malic acid, succinic acid, pamoic acid, sulfuric acid and phosphoric acid.

The (S)-isomers of Formula I can be administered orally, rectally, parenterally, or transdermally, alone or in combination with other psychostimulants, antidepressants, and the like to a patient in need of treatment. Oral dosage forms include tablets, capsules, dragees, and similar shaped compressed pharmaceutical forms. Isotonic saline solutions containing 20–200 milligrams/milliliter can be used for parenteral administration which includes intramuscular, intrathecal, intravenous and intra-arterial routes of administration. Rectal administration can be effected through the use of suppositories formulated from conventional carriers such as cocoa butter. Transdermal administration can be effected through the use of transdermal patch delivery systems and the like. The preferred routes of administration are oral and parenteral.

The dosage employed must be carefully titrated to the patient, considering age, weight, severity of the condition, and clinical profile. Typically, the amount of (S)-mexiletine administered will be in the range of about 50–600 mg/day, or more preferably 150–450 mg/day, but the actual decision as to dosage must be made by the attending physician.

The following examples will serve to further typify the nature of the invention, but should not be construed as a limitation on the scope thereof, which is defined solely by the appended claims.

Subjects:

Rats (male Sprague Dawley, Harlan Industries, Indianapolis, Ind.) are housed in ALAC approved cages using soft bedding and 12/12 hour day/night cycle, in atmospherically maintained rooms in the CTF/VA Animal Vivarium. For the nerve ligation model, rats are typically lesioned at 125–175 g body weight, while for the diabetic rat model, 275–325 gram rats are employed.

EXAMPLE 1

Pain Model

Nerve Ligation Model

Male Harlan Sprague Dawley rats (275-325g) were used for testing the isomers of mexiletine and lidocaine in a neuropathic pain state experimental model according to the method of Kim and Chung. Kim SH, Chung JM: *An experimental model for peripheral neuropathy produced by segmental spinal nerve ligation in the rat. Pain* 50: 355–363 (1992).

Anomalous pain states evoked by nerve injury in man is believed to be modeled by effects produced by chronic peripheral nerve injury lesion in rats. To create a chronic nerve injury the L5 and L6 spinal nerves are visualized by removal of the L6 transverse process. The two spinal nerves are ligated with 6-0 silk thread to the dorsal root ganglion under halothane anesthesia. This procedure leads to the generation of spontaneous pain and mechanical allodynia within 24 hours of the injury. The rats were allowed a 7 day postoperative recovery period before further studies or procedures.

EXAMPLE 2

Pain Model

Streptozotocin Diabetic Rat Model

Rats are made diabetic by a single intraperitoneal injection of streptozotocin (50 mg/kg body weight) freshly dissolved in 0.9% sterile saline) in order to ablate pancreatic β cells and induce insulin deficiency. Two days later, diabetes is confirmed in streptozotocin-injected rats by measuring glucose concentration in a blood sample obtained by tail prick, using a glucose oxidase-impregnated test strip and reflectance meter (Ames Glucostix and Glucometer II, Myles Inc., Elkhart, Ind.) (Calcutt, et al., 1993). Streptozotocin-injected animals with blood glucose concentrations below 15 mmol/l are excluded from subsequent studies. Diabetic rats received thrice weekly sub-cutaneous injections of 2U heat-treated Ultralente insulin (Novo Industrie A/C, Copenhagen, Denmark) in a regime shown to prevent loss of body weight and musculature whilst allowing continued hyperglycemia. Injections were made on Monday, Wednesday and Friday and behavioral measurements made on Tuesdays and Thursdays.

EXAMPLE 3

Behavioral Testing

Rats were placed in a clear plastic, wire mesh-bottomed cage, divided into individual compartments of 5×6×9 inches, which permitted freedom of movement while allowing access to the paws to be tested. Animals were allowed to accommodate to this environment for approximately 15 minutes, or until cage exploration behavior ceased. To assess the 50% mechanical threshold for paw withdrawal, von Frey hairs were applied to the plantar mid-hindpaw, avoiding the footpads. The eight von Frey hairs used are designated by and range from 0.4–15.1 grams (#'s3.61–5/18). Each hair was pressed perpendicularly against the paw with sufficient force to cause bending, and held for approximately 6–8 seconds. A positive response was noted if the paw was sharply withdrawn. Absence of a response was cause to present the next consecutive stronger stimulus: a positive response was cause to present the next weaker stimulus. If a change in response occurred, causing a change in the direction of stimulus presentation from descending to ascending or vice-versa, four additional data points were collected subsequent to the change. Stimuli were presented successively until either six data points were collected, or the maximum or minimum stimulus was reached. If a minimum stimulus was reached and positive responses still occurred, the threshold was assigned an arbitrary minimum value of 0.25 grams; if a maximum stimulus was presented and no response occurred, a maximum threshold value of 15 grams was assigned. The resulting pattern of responses was tabulated and the 50% response threshold computed using the formula:

$$\log(\text{threshold, mg} \times 10) = Xf + k\partial$$

Where $Xf$=values of last von Frey hair applied;

$k$=correction factor based on pattern of responses;

$\partial$=mean distance in log units between stimuli.

Based on observations on normal, unoperated rats and sham-operated rats, the cutoff of a 15.1 g hair is selected as the upper limit for testing. (Chaplan, et al., 1994.)

EXAMPLE 4

Drug Treatment

Four agents were examined. 1)(R)-mexiletine; 2) (S)-mexiletine; 3) (R,S)-mexiletine; 4) lidocaine (positive control), in addition to saline (vehicle control). The dose range was determined on a single rat on a 0.5 log unit dose until an endpoint of effect was reached (loss of motor function, seizure/rigidity, complete nerve blockage). Once the dose range was established, each drug was examined at a minimum of 3 doses in groups of 6 rats per dose. Groups were prepared to receive injections of drugs, or saline control, by i.p. injection. After the animals accommodated to the post-operative test environment, animals received treatment and the effects upon the tactile threshold were determined using the up-down method as described in Example 3. The following is a typical paradigm for IP application:

| Time | −15 | 0 | 15 | 30 | 60 | 90 | 120 min | 24 hrs |
|---|---|---|---|---|---|---|---|---|
| Treat/Eval | Test | Inject | Test | Test | Test | Test | Test | Test |

EXAMPLE 5

Anti-allodynic Effect in Chung Model

Table I provides results of drug treatment in the Chung Model prepared in accordance with Example 1 and tested in accordance with the paradigm described in Examples 3 and 4.

TABLE I

| Drug | Lidocaine | S-Mexiletine | R-Mexiletine | RS-Mexiletine |
|---|---|---|---|---|
| Max. usable dose (mg/kg) | 60 | 30 | 30 | 30 |
| Max. efficacy (% MPE) | 83 | 79 | 12 | 76 |
| ED 50 (mg/kg) | 38 | 14 | — | 35 |
| Time to peak effect (min) | 15 | 15 | 30 | 15–30 |

TABLE I-continued

| Drug | Lidocaine | S-Mexiletine | R-Mexiletine | RS-Mexiletine |
|---|---|---|---|---|
| Duration (min) | 90 | 60 | — | 60 |

The maximum efficacy or highest % suppression of allodynia at highest dose tested was greatest for (S)-mexiletine 79%±11% of maximum possible effect compared to 12%±5% for (R)-mexiletine. The ED 50 or the calculated dose for 50% suppression was 14 mg/kg vs 35 mg/kg racemate. The ED 50 for the(R)-mexiletine could not be calculated due to low effect at maximum dose.

EXAMPLE 6

Anti-allodynic Effect in Diabetic Model

Table II provides results of drug treatment in the Diabetic Model prepared in accordance with Example 2 and tested in accordance with the paradigm described in Examples 3 and 4.

TABLE II

| Drug Dose (mg/kg) | S-Mexiletine % MPE | R-Mexiletine % MPE | RS-Mexiletine % MPE |
|---|---|---|---|
| 3 | 12 | 10 | 20 |
| 10 | 50 | 15 | 29 |
| 20 | 30 | 11 | 42 |
| 30 | 75 | 86 | 75 |

Animals prepared in accordance with the diabetic model exhibited behavioral problems which affected the outcome of this study, especially at higher dosages. The diabetic animals exhibited shorter duration (time to peak) due to rapid clearance of the drug caused by the induced diabetic condition. In addition, the diabetic animals were more sensitive to the drug treatment and at higher doses suffered toxicity effects unrelated to the isomer study. It has been concluded that the data obtained from the highest dosage (30 mg/kg) was detrimentally affected by these behavioral problems and thus, the results not probative of the efficacy of either isomer at higher dosages. Accordingly, Table III was prepared using only 3, 10 and 20 mg/kg dosage levels which do not appear to have been affected by the toxicity problems.

TABLE III

| Drug | Lidocaine | S-Mexiletine | R-Mexiletine | RS-Mexiletine |
|---|---|---|---|---|
| Max. usable dose (mg/kg) | 20 | 20 | 20 | 20 |
| Max. efficacy (% MPE) | 39 | 65 | 11 | 61 |
| ED 50 (mg/kg) | 32 | 15 | — | 17 |
| Time to peak effect (min) | 30 | 15–45 | 15–30 | 30–45 |
| Duration (min) | 30 | 60 | — | <60 |

These results conform to those of the Chung model. The maximum efficacy or highest % suppression of allodynia at highest dosage unaffected by toxicity was greater for (S)-mexiletine 65%±16% of maximum possible effect to 11%±5% for (R)-mexiletine.

EXAMPLE 7

Preparation of Gelatin Dry Filled Capsule

Gelatin dry filled capsules, each containing 100 milligrams of (S)-mexiletine, can be prepared in the following manner:

| Composition (for 1000 capsules) | |
|---|---|
| (S)-mexiletine HCl | 100 g |
| Avicel pH 102 NF | 200 g |
| Magnesium stearate | 5.0 g |
| Starch NF | 190 g |
| Sodium lauryl sulfate | 5.0 g |

The sodium lauryl sulfate is sieved into the (,S)-mexiletine through a sieve of 0.2 mm mesh and the two components are intimately mixed for 10 minutes. The avicel microcrystalline cellulose is then added through a sieve of 0.9mm mesh and the whole is again intimately mixed for 10 minutes. The starch is then added through a sieve of 0.9 mm and the whole is again intimately mixed for 10 minutes. Finally the magnesium stearate is added through a sieve of 0.8 mm width and, after mixing for a further 3, the mixture is introduced in portions of 500 mg each into size 1 gelatin dry-fill capsules.

EXAMPLE 8

Preparation of Transdermal System

A transdermal system was fabricated by the following procedure. A pressure sensitive adhesive was prepared by casting an acrylic adhesive solution onto a siliconized polyethylene teraphthlate sheet (3M #1033). The solvent was evaporated in a 95° C. forced air oven for 30 minutes. The resultant film, 75 microns thick, was laminated to another polyester film (3M Cotran 9710). This three layer assembly was peripherally heat sealed to aluminized polyester backing (3M Sccotchpak® 1006) forming delivery devices with an active releasing area of 20 cm. A 30 wt % solution of (S)-mexiletine in 38 wt % isopropyl alcohol, 30 wt % water, and 1.2 wt % isopropyl myristate is prepared. The solution is gelled with 0.5 wt % hydroxypropyl-cellulose. The reservoir of the patch is filled with the gelled (S)-mexiletine solution through an opening in the heat seal. The opening is sealed closed after filling.

EXAMPLE 9

Preparation of Tablets

Tablets can be made by mixing the (S)-mexiletine with one or more pharmaceutically acceptable excipients and forming a tablet. For example, tablets each containing 100 mg of (S)-mexiletine HCl can be prepared in the following manner:

| Composition (for 1000 tablets) | |
|---|---|
| (S)-Mexiletine HCl | 100 grams |
| Lactose | 250 grams |
| Corn Starch | 17.5 grams |
| Polyethylene Glycol 6000 | 5.0 grams |
| Talc | 25 grams |
| Magnesium Stearate | 4.0 grams |
| Demineralized Water q.s. | |

The solid ingredients are first forced through a sieve of 0.6 mm mesh width. Then the (S)-mexiletine HCl, lactose, talc, magnesium stearate, and half the starch are intimately mixed. The other half of the starch is suspended in 60 ml of water and this suspension is added to a boiling solution of the polyethylene glycol in 260 ml of water. The resulting paste is added to the pulverulent substances, and the whole is mixed and granulated, if necessary with addition of water. The granule is dried overnight at 35° C., forced through a sieve of 1.2 mm mesh width and compressed to form tablets of approximately 15 mm diameter which are concave on both sides and have a breaking notch on the upper side.

What is claimed is:

1. A method of treating painful neuropathies comprising administering a therapeutically effective amount of a pharmaceutical compound comprising the (S)-isomer of a chiral compound having the formula:

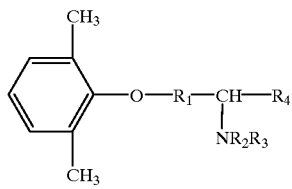

wherein R1 is C1–C5 hydrocarbyl, R2 and R3 are independently C1–C5 hydrocarbyl or H, R4 is C1–C5 hydrocarbyl, R3 and R4 may optionally be joined together to form a 5, 6 or 7 membered ring system, or a pharmaceutically acceptable salt thereof, substantially free of the (R)-isomer.

2. The method of claim 1 wherein R1 is CH2, R2 and R3 are each H, and R4 is C1–C5 alkyl.

3. The method of claim 2 wherein R4 is CH3.

4. The method of claim 1 wherein the amount administered of the pharmaceutical compound is about 50 mg to 600 mg per day.

5. The method of claim 1 wherein the amount of (S)-isomer is greater than 99% by weight of the total amount of the chiral compound.

* * * * *